United States Patent
Wang et al.

(10) Patent No.: US 7,679,504 B2
(45) Date of Patent: Mar. 16, 2010

(54) SYSTEM AND METHOD OF DISCOVERING, DETECTING AND CLASSIFYING ALARM PATTERNS FOR ELECTROPHYSIOLOGICAL MONITORING SYSTEMS

(75) Inventors: Xi Wang, Niskayuna, NY (US); Timothy L. Johnson, Niskayuna, NY (US); Stephen T. Treacy, Milwaukee, WI (US)

(73) Assignee: General Electric Company, Niskayuna, NY (US)

( * ) Notice: Subject to any disclaimer, the term of this patent is extended or adjusted under 35 U.S.C. 154(b) by 384 days.

(21) Appl. No.: 11/749,400

(22) Filed: May 16, 2007

(65) Prior Publication Data

US 2008/0284582 A1    Nov. 20, 2008

(51) Int. Cl.
*G08B 26/00* (2006.01)
*G08B 29/00* (2006.01)
*A61B 5/00* (2006.01)

(52) U.S. Cl. .......... 340/506; 340/507; 340/521; 340/522; 340/523; 340/525; 600/301; 700/21

(58) Field of Classification Search .......... 340/506, 340/505, 523
See application file for complete search history.

(56) References Cited

U.S. PATENT DOCUMENTS

| | | | |
|---|---|---|---|
| 4,977,390 A * | 12/1990 | Saylor et al. | 340/521 |
| 6,024,699 A | 2/2000 | Surwit et al. | |
| 6,690,274 B1 * | 2/2004 | Bristol | 340/506 |
| 6,804,656 B1 | 10/2004 | Rosenfeld et al. | |
| 6,988,989 B2 | 1/2006 | Weiner et al. | |
| 2002/0055790 A1 * | 5/2002 | Havekost | 700/80 |
| 2004/0068332 A1 * | 4/2004 | Ben-Gal et al. | 700/51 |
| 2005/0108384 A1 * | 5/2005 | Lambert et al. | 709/224 |
| 2006/0192667 A1 * | 8/2006 | Al-Ali | 340/511 |
| 2007/0032705 A1 | 2/2007 | Ali | |

OTHER PUBLICATIONS

Chambrin, M.C., P. Ravaux, D. Calvelo-Aros, et al., "Multi-centric study of monitoring alarms in the adult intensive care unit (ICU): a descriptive analysis", J. Intensive Care Med, vol. 25: pp. 1360-1366. (1999).

Tsien, C. L. And J. C. Fackler. "Poor prognosis for existing monitors in the intensive care unit." Critical Care Medicine 25: 614-619, (1997).

Johsnon et al, "System and Method for Providing Centralized Physiological Monitoring"; U.S. Appl. No. 11/567,758, filed Dec. 7, 2006.

* cited by examiner

*Primary Examiner*—Donnie L Crosland
(74) *Attorney, Agent, or Firm*—Scott J. Asmus

(57) ABSTRACT

A system and method for electrophysiological monitoring system including a plurality of sensors configured to detect one or more health parameters of a patient and a monitoring device configured to receive a plurality of sensing signals from the sensors and output a monitoring signal representative of an alarm sequence, wherein the alarm sequence comprises a set of alarm events identified in the sensing signals. The system also includes an on-line monitoring module configured to generate a suffix tree data structure in response to the monitoring signal to identify alarm patterns from the set of alarm events and classify the alarm sequence in response to the occurrences of alarm patterns in the alarm sequence. The on-line monitoring module is further configured to alert monitoring personnel of an alarm condition after processing the alarm sequence in real-time.

21 Claims, 6 Drawing Sheets

SYSTEM AND METHOD OF DISCOVERING, DETECTING AND CLASSIFYING ALARM PATTERNS FOR ELECTROPHYSIOLOGICAL MONITORING SYSTEMS

BACKGROUND OF THE INVENTION

The present invention relates generally to discovering, classifying and detecting alarm patterns and more particularly, to a method of discovering, classifying and detecting alarm patterns for electrophysiological monitoring systems.

Monitoring personnel, such as a physician or nurse, may use an electrophysiological monitoring system to simultaneously monitor multiple health parameters such as blood pressure, heart rhythm, heart rate, and specific oxygen to determine a health condition of a patient. Typically, electrophysiological monitoring systems raise alarms when a monitored signal value crosses a threshold. Alarms may also be raised when a specific waveform or waveform property is detected in a short segment of a recorded signal, e.g., a moving window average. For example, if a patient's heart rate exceeds a certain level or threshold, an alarm may be recognized and generated.

With such traditional detection methods, too many alarms may be generated to be of medical significance. That is, one alarm for a particular patient condition may be insignificant on its own. However, when the alarm is found in a sequence or group of alarms, it may indicate a particular patient health condition. Additionally, when insignificant alarms are generated, medical staff time is frivolously utilized in investigating such alarms, and when too many insignificant alarms are generated, medical staff may begin to ignore or to place a low priority in such alarms. When this occurs, a valid alarm may be ignored or treated with less urgency during a critical period, thus endangering the patient. Furthermore, additional non-critical alarms may be recognized due to faulty sensors, equipment malfunctions, or patient movement. These "non-actionable alarms" divert resources of medical personnel to non-critical alarms and reduce the efficiency of the monitoring process.

Therefore it would be beneficial to discover and detect alarm patterns in an alarm sequence to identify critical health conditions in order to reduce the number of non-critical alarms. However, known alarm pattern detection methods are based on time series signal processing methods that may fail to discover and/or recognize certain alarm patterns that are extended over a long period of time. In addition, alarm patterns may not be properly detected if they are interrupted by another non-critical alarm also referred to as an 'interdigitated alarm.' Furthermore, known alarm pattern detection methods may only detect a critical medical condition after the entire alarm sequence is completed.

Therefore, it would be beneficial to design an alarm pattern discovery, detection, and classification method that reduces the number of non-critical alarms, discovers alarm patterns from multiple concurrent and sequential alarm signals over an extended period of time, and can classify an alarm sequence with a medical condition before the alarm sequence is complete.

BRIEF DESCRIPTION OF THE INVENTION

The present invention is a directed method for discovery, classification and detection of alarm patterns for electrophysiological monitoring systems that overcomes the aforementioned drawbacks. A suffix substring data structure is used to discover alarm patterns in an alarm sequence. More specifically, discovery of alarm patterns from monitoring multiple alarm signals, efficiently detecting patterns in real-time, and the ability to associate physiological alarm pattern data with a health status of a patient in response to alarm type incident rates.

According to an aspect of the present invention, an electrophysiological monitoring system including a plurality of sensors configured to detect one or more health parameters of a patient and a monitoring device configured to receive a plurality of sensing signals from the sensors and output a monitoring signal representative of an alarm sequence, wherein the alarm sequence comprises a set of alarm events identified in the sensing signals. The system also includes an on-line monitoring module configured to generate a suffix tree data structure in response to the monitoring signal to identify alarm patterns from the set of alarm events and classify the alarm sequence in response to the occurrences of alarm patterns in the alarm sequence. The on-line monitoring module is further configured to alert monitoring personnel of an alarm condition after processing the alarm sequence in real-time.

According to another aspect of the present invention, a method for electrophysiological monitoring includes receiving a monitoring signal derived from a patient wherein the monitoring signal provides an alarm sequence, developing a suffix substring data structure to identify a plurality of alarm patterns from the alarm sequence, and generating an incidence vector that determines a relative incidence of each type of alarm pattern with respect to the plurality of alarm patterns in the alarm sequence. The method further includes grouping the incidence vector in a cluster using a clustering algorithm, classifying one or more patients according to their pattern incident rates which are obtained by extraction of alarm patterns and storing the classification of the incidence vector in a database.

According to yet another aspect of the present invention, a method for electrophysiological monitoring includes receiving a monitoring signal from a patient wherein the monitoring signal provides an alarm sequence, wherein the alarm sequence includes at least one alarm pattern. The method also includes developing a suffix substring data structure in real-time to identify alarm patterns of medical interest contained in the alarm sequence and generating an incidence vector in response to the suffix substring data structure. The alarm sequence is classified to a classification cluster using a classification algorithm based on the incidence vector and monitoring personnel is alerted to indicate a condition corresponding to the cluster after processing the alarm sequence in real-time.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

DETAILED DESCRIPTION OF THE PREFERRED EMBODIMENT

References throughout this specification to "one embodiment," "an embodiment," "one example," or "an example" mean that a particular feature, structure, or characteristic described in connection with the embodiment is included in at least one embodiment of the present invention. Thus, the appearances of the phrases "in one embodiment," "in an embodiment," "in one example," or "in an example" in various places throughout this specification are not necessarily all referring to the same embodiment. The particular features, structures or characteristics may be combined for example into any suitable combinations and/or sub-combinations in one ore more embodiments or examples. Furthermore, the particular features, structures, or characteristics may be included in an integrated circuit, an electronic circuit, a process (shared, dedicated, or group) and memory that execute one or more software or firmware programs, a combinational logic circuit, or other suitable components that provide the described functionality.

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Figure 1:
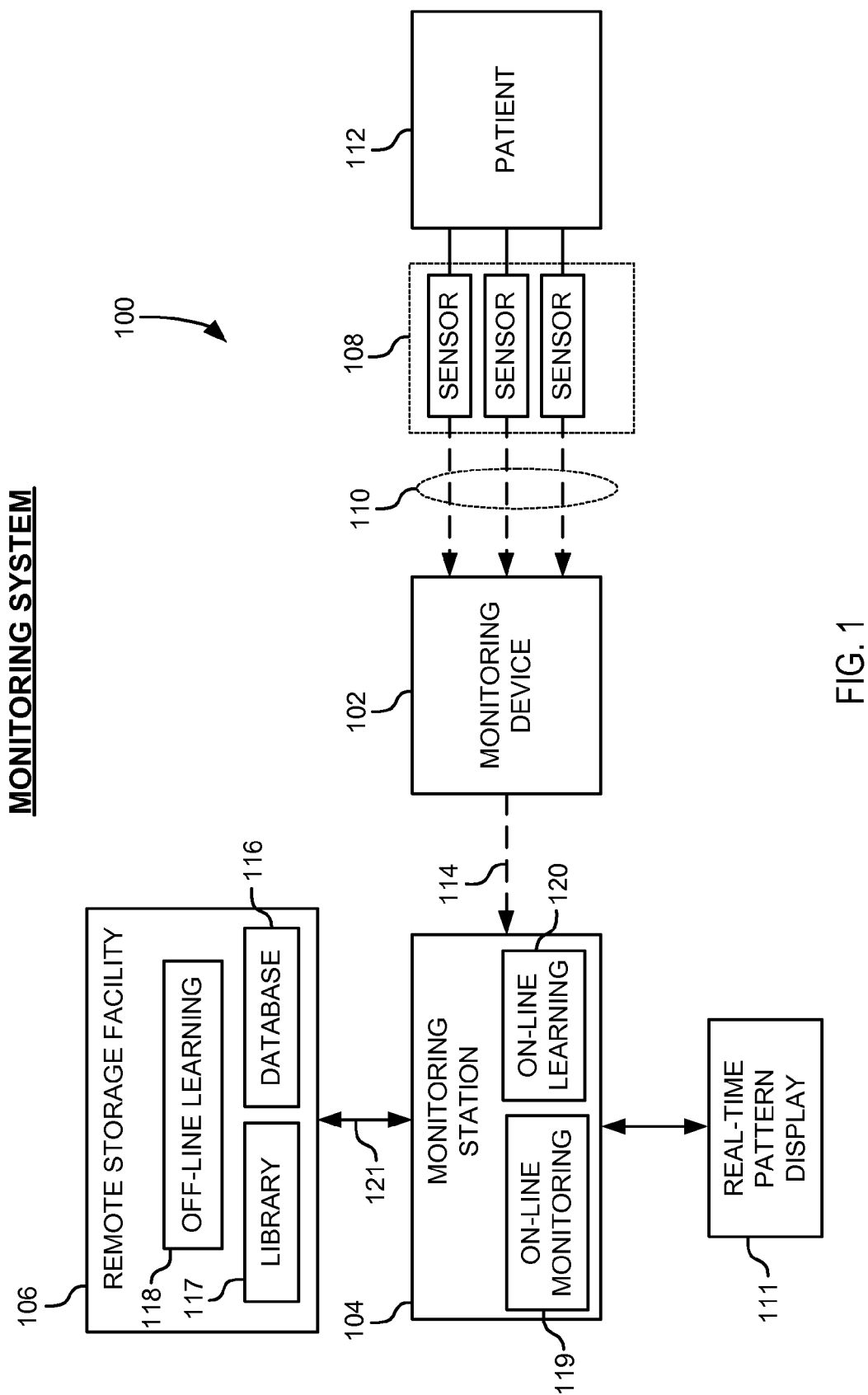
FIG. 1 is an example functional block diagram of a patient monitoring system according to an embodiment of the present invention.

FIG. 1 shows a functional block diagram of a monitoring system 100. System 100 includes a monitoring device 102, a monitoring station 104, a remote storage facility 106, a plurality of sensors 108, and a real-time pattern display 111. The monitoring device 102 receives a plurality of sensing signals 110 from sensor 108. In one embodiment, the monitoring device 102 may be APEX PRO™ by GE Healthcare. The monitoring device 102 outputs a waveform monitoring signal 114 in response to the sensing signals 110. As shown, sensors 108 are coupled to patient 112 to monitor and detect health parameters such as, heart rate, heart beat, blood pressure, specific oxygen, blood sugar, or the like. In one embodiment, the patient 112 may be a human or other animal such as, a cat or a dog. The sensors 108 or monitoring device 102 may be wireless sensors that transmit sensing signals 110 through a wireless network. As shown, the monitoring signal 114 is received by monitoring station 104 in order to detect alarms and classify alarm patterns and store them in an alarm pattern database 116. Database 116 may incorporate a chronological alarm log file containing all alarm times and types during one or more monitored sessions.

Monitoring station 104 includes an on-line monitoring module 119 and an on-line learning module 120. The on-line monitoring module 119 monitors a patient's physiological status and alerts monitoring personnel when an alarm pattern of significance has been detected via a real-time pattern display 111 that is used by monitoring personnel to view alarm sequence of the patient 112. In one embodiment, the real-time pattern display 111 may be included in monitoring device 102 or in monitoring station 104. In one embodiment, monitoring station 104 alerts a user, such as a physician, nurse, or other qualified medical personnel when an alarm or alarm pattern from database 116 is recognized in the monitoring signal 114. The alert may be displayed to the user on the real-time pattern display 111. In addition, monitoring station 104 or real-time pattern display 111 may generate an audible alert. Monitoring station 104, with real-time display 111 may also generate a table or graph showing recorded alarm patterns of interest for the patient 112 for a user on real-time pattern display 111. In this manner, a physician or other medical practitioner may review patient 112 for a particular period. In one embodiment, the monitoring signal 114 may be multiple signals. In another embodiment, the monitoring station 104 may be coupled to receive a monitoring signal 114 from multiple patients. In one embodiment, the monitoring station 104 may be located in a hospital, clinic, or other medical facility and/or location where monitoring personnel may monitor patient 112 such as a monitoring facility.

As shown in FIG. 1, the remote storage facility 106 is connected to the monitoring station 104 through a communications link 121 and is configured to communicate with, receive, and store the detected alarm patterns identified by the monitoring station 104. More specifically, the remote storage facility 106 includes alarm pattern database 116 and an alarm pattern library 117, which may be accessed in real-time to compare alarm patterns in the monitoring signal 114 with stored alarm patterns in alarm pattern library 117. Additionally, the monitoring station 104 includes an off-line learning module 118 that recognizes and stores alarm sequences while processing electrical medical records to further increase and/or diagnose more physiological states.

Figure 2:
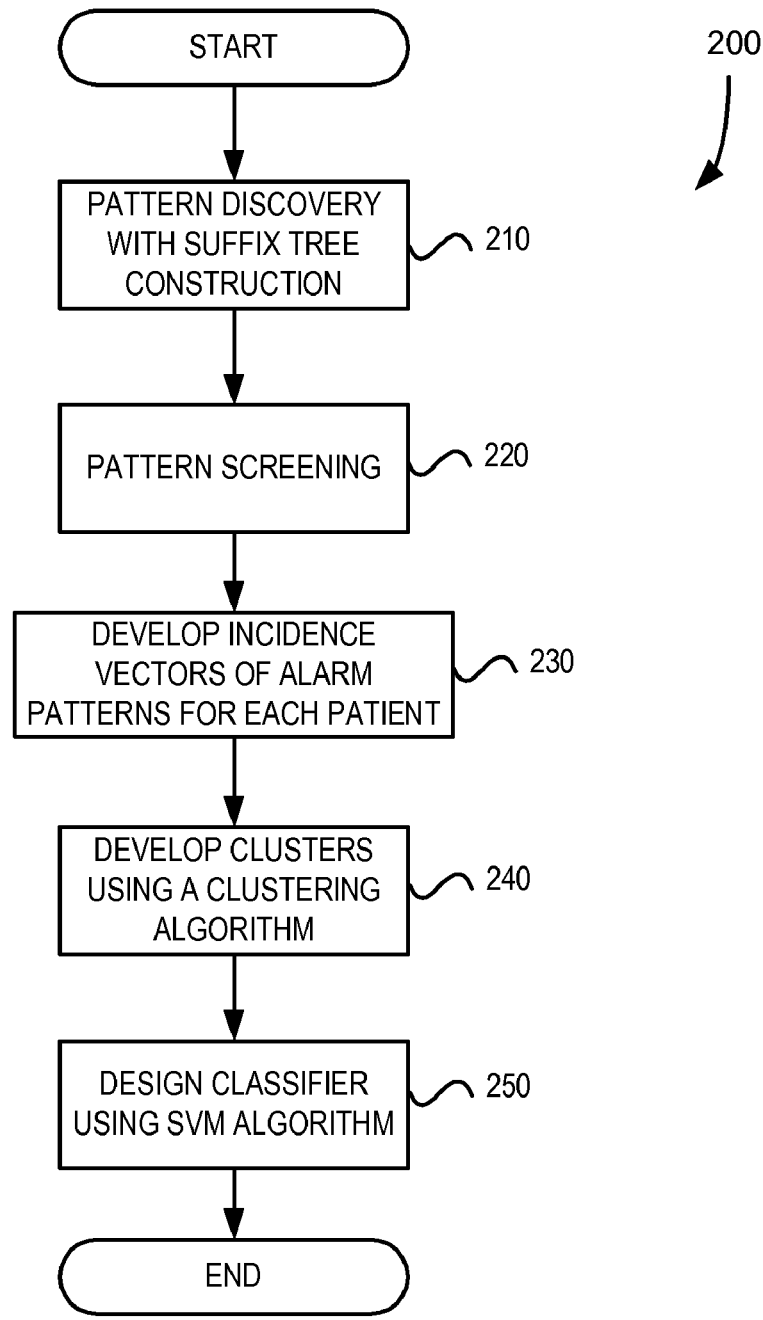
FIG. 2 is an example flowchart of an off-line method for detecting and classifying patient alarm patterns according to another embodiment of the present invention.

FIG. 2 is a flowchart 200 of an off-line method for discovering and classifying patient alarm patterns according to an embodiment of the present invention. In one example, the flowchart 200 may be implemented in off-line learning module 118 of FIG. 1. In block 210, a pattern discovery algorithm is implemented by generating a suffix tree data structure to find alarm patterns from multiple patients. More specifically, the suffix tree data structure is used in the pattern discovery algorithm to identify and store new alarm patterns in alarm sequences, in which many alarm patterns may go undetected using traditional alarm pattern detection methods.

Figure 5:
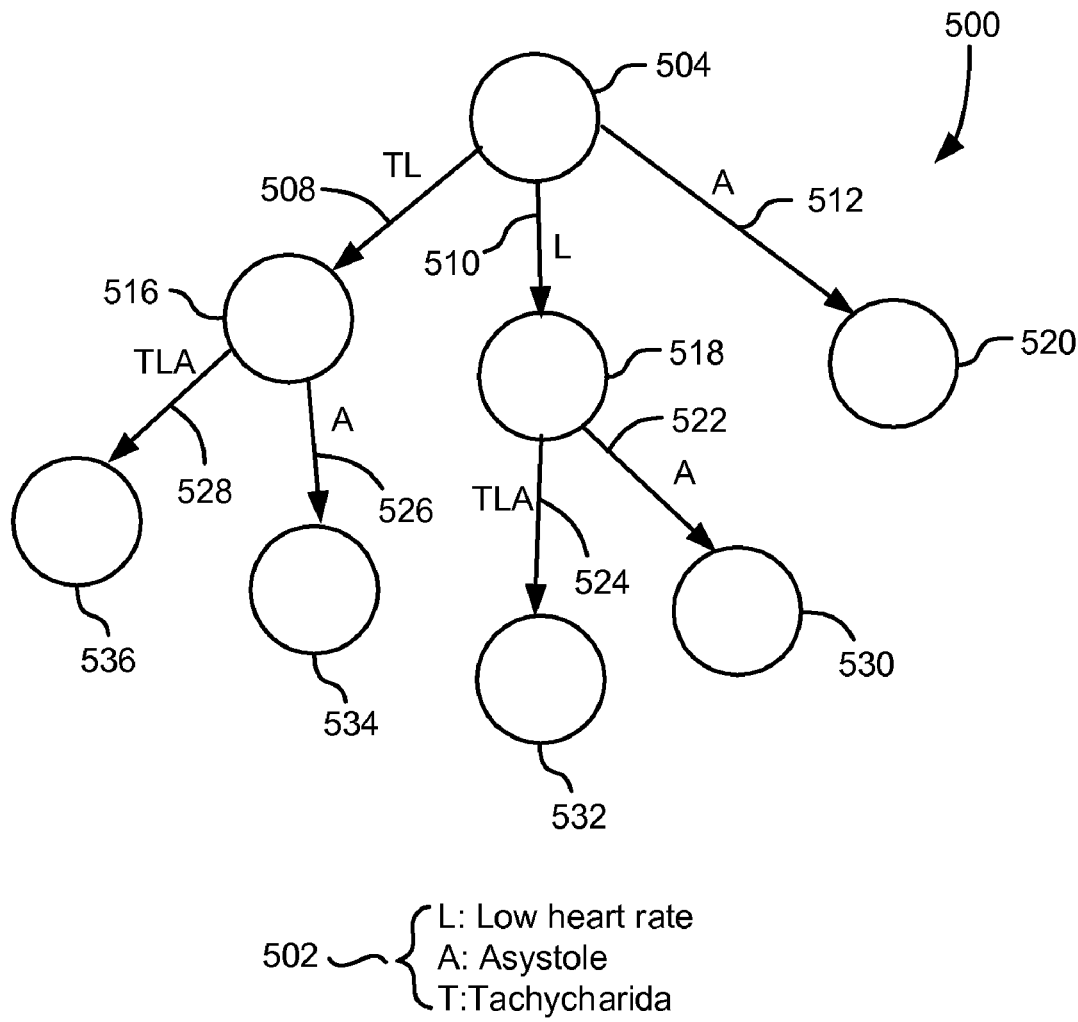
FIG. 5 is an example diagram illustrating a suffix tree data structure according to an embodiment of the present invention.

FIG. 5 illustrates an example suffix tree data structure 500 according to the teachings of the present invention. In the suffix tree data structure 500, several alarm types 502 of interest are considered for detecting alarm patterns in an alarm sequence. More specifically the alarm types 502 considered are, a low heart rate event that is represented by a letter 'L', an asystole event that is represented by the letter 'A', and a tachycardia event that is represented by the symbol 'T.'

The suffix tree data structure 500 includes a central node 504, a plurality of first stems 508, 510, and 512, a plurality of first leaves 516, 518, and 520, a plurality of second stems 522, 524, 526, and 528, and a plurality of second leaves 530, 532, 534, and 536. Each first leaves 516, 518 and 520 and each second leaves 530, 532, 534, and 536 are associated with a specific alarm pattern. For example, first leaf 508 is generated when an alarm pattern 'TL' is first recognized from an alarm sequence. Another example, second leaf 532 is generated when an alarm pattern 'TLTLA' is first recognized. By using a suffix tree data structure any distinct alarm pattern that occurs in the alarm sequence will generate a stem, also referred to as a pathway, to a new leaf specific to that alarm pattern. If a substring of an alarm pattern is common to another alarm pattern, then a stem will be generated from that leaf to another leaf. For example, an alarm pattern 'TL' represented by leaf 516 is a substring that is common to the alarm pattern 'TLTLA' represented by second leaf 536. Since 'TL' is common to the alarm pattern TLA, second stem 528 is generated from first leaf 516 to generate second leaf 536. If an alarm pattern has already been identified by the suffix tree data structure 500, the number of occurrences for the alarm pattern type corresponding to a patient history will be accounted for with an incidence vector, which is discussed in further detail below. In an alternate embodiment, the repeated occurrences of alarm patterns may be accounted for by weighting the nodes of the suffix tree data structure 500. For example, if pattern type 'LTLA' occurs five times then second leaf 532 and pattern type 'LA' occurs three times, then first leaf 518 that is representative of 'L' will be weighted more than second leaf 532 and 530. Since 'L' is a common substring of 'LA' and of 'LTLA' first leaf 518 is weighted value equal to the sum of the weighted value of second leafs 532 and 530. In summary, the leaf that corresponds with the alarm pattern generated when a new alarm pattern is identified and is weighted in response to the number of times the alarm pattern is recognized.

One of the realized benefits of the suffix tree data structure 500, is to find common alarms from a pool of patients with similar histories, also referred to as electric patient medical records (EMR). According to an embodiment of the present invention, a longest common substring may be detected with a suffix tree data structure 500 in order to identify common alarm patterns. More specifically, a longest common substring is defined as the longest string that is a substring of two or more strings. For example, the longest common substring in suffix tree data structure 500 is 'TL' which corresponds with first stem 508 and first node 516. In one embodiment, more than one longest common substring may be determined in a suffix tree data structure.

In one embodiment, a least common substring is determined to determine the alarm pattern or patterns that are the shortest that are common to all patients in a class (i.e., disease category or medical condition). In one example, this may be used to distinguish a rare medical event and/or condition. In one embodiment, a longest common subsequence is determined. More specifically, a longest common subsequence is defined as a longest sequence such as a subsequence of all sequences in a set of sequences. In one example, the longest common subsequence may be set to a maximum and/or a minimum length that is to be identified.

Referring back to flowchart 200 in FIG. 2, in block 220, the alarm patterns are screened for relevant alarms. More specifically, the alarm patterns may be screened, but not limited to, the longest common substring, the least common substring and the longest common subsequence. This allows certain alarm events that may be irrelevant such as sensor failures, patient movement, or independent alarm events that have no significance, to be excluded from the alarm patterns of interest.

Figure 6:
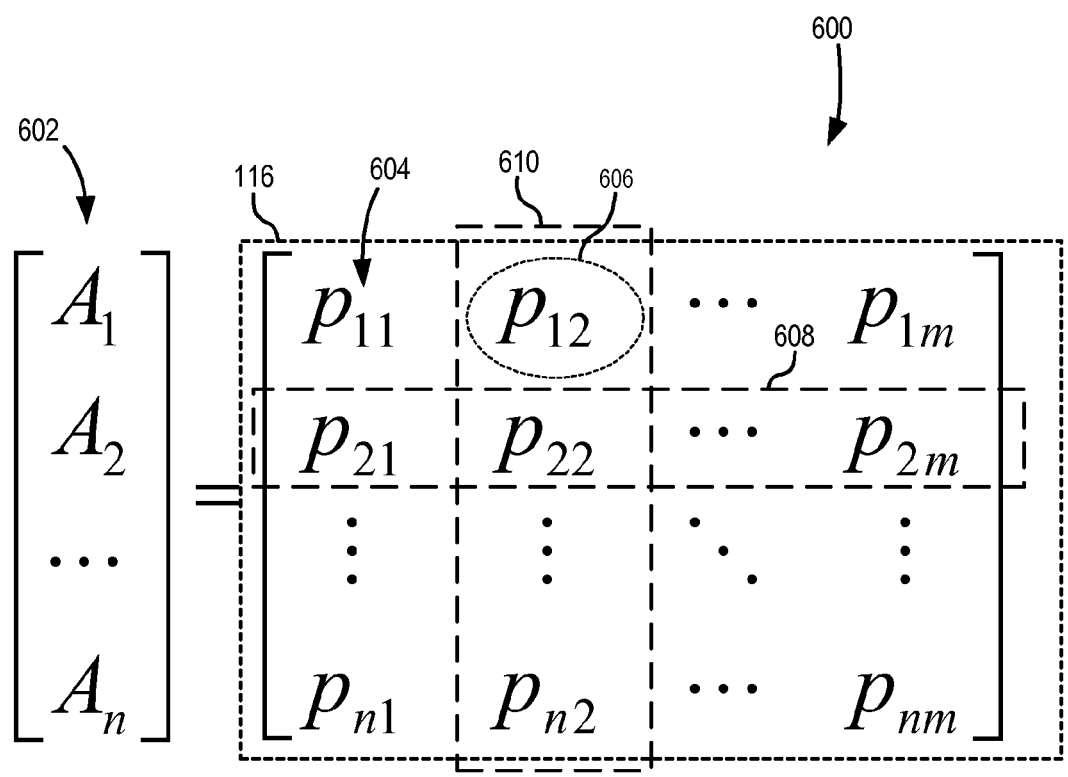
FIG. 6 is an example diagram of a plurality of incidence vectors contained in a pattern database, according to an embodiment of the present invention.

In block 230, multiple incidence vectors of alarm patterns, each corresponding to a patient recording session, are determined. In one example, each incidence vector determines the relative frequency of occurrence of an alarm pattern type with respect to all the alarm pattern type that occur in the alarm sequence of a particular patient or patient class. As shown in FIG. 6, a series of incidence vectors 602 may be calculated from occurrence values 604 in alarm pattern library 116. Each occurrence value 604 is representative of a ratio of the number of occurrences of an alarm pattern 'm' over the total number of alarm pattern occurrences for patient 'n,' where 'n' is representative of a patient and 'm' is representative of an alarm pattern or alarm pattern type. For example, occurrence value 606 is representative of a ratio of the number of occurrences of an alarm pattern '2' over the total number of alarm pattern occurrences for patient '1'.

Still referring to FIG. 6, in the alarm pattern library 116, each row 608 of occurrence values 604 corresponds to a respective incidence vector 602 and each column 610 of occurrence values 604 corresponds to a specific alarm pattern. Multiple occurrence values 604 make up the incidence vector 602. Each incidence vector 602 establishes a relative incidence of alarm pattern type with respect to the corresponding alarm sequence during an entire patient monitoring session.

Referring back to flowchart 200 in FIG. 2, in block 230, multiple incidence vectors 602 are determined. In one example, flow chart 200 may be implemented in off-line learning module 118. In block 240, a clustering algorithm is used to group incidence vectors representative of alarm sequences together. More specifically, clustering is the classification of objects into different groups, or more precisely, the partitioning of a data set into subsets (clusters) such that the data in each subset share some common trait (in this case common pattern incidence rates). Clustering is beneficial for scalability, defining arbitrary boundaries of a group, ability to deal with noise or outliers, insensitivity to order of input, and high dimensionality (number of patients). In the preferred embodiment, a K-means clustering algorithm is used which is known to one skilled in the art. In other embodiments, other clustering algorithms such as, but not limited to, hierarchical, Fuzzy-C means, or "mixture-of-Gaussians" clustering algorithms may be used. In block 250, designing a classifier for clusters of incidence vectors is accomplished using a support vector machine (SVM) algorithm. More specifically, the SVM algorithm will associate alarm pattern statistics with, a particular cluster associated with disease, type of medical condition, and/or general state of health, which is a method of unsupervised learning. For example, the International Classification of Diseases (ICD) includes a taxonomy of cardiac and cardiac-relate diseases and may be used to classify existing electric medical records. In another embodiment, a supervised learning process may classify the incidence vectors. For example, once the clusters have been developed, one or more qualified medical personnel, such as a physician(s), may asses the incidence vectors of alarm sequences to classify each cluster. One benefit of using the SVM algorithm is to efficiently classify non-normally distributed clusters with multi-dimensional data, the dimensions being the number of patterns that are to be classified.

Figure 3:
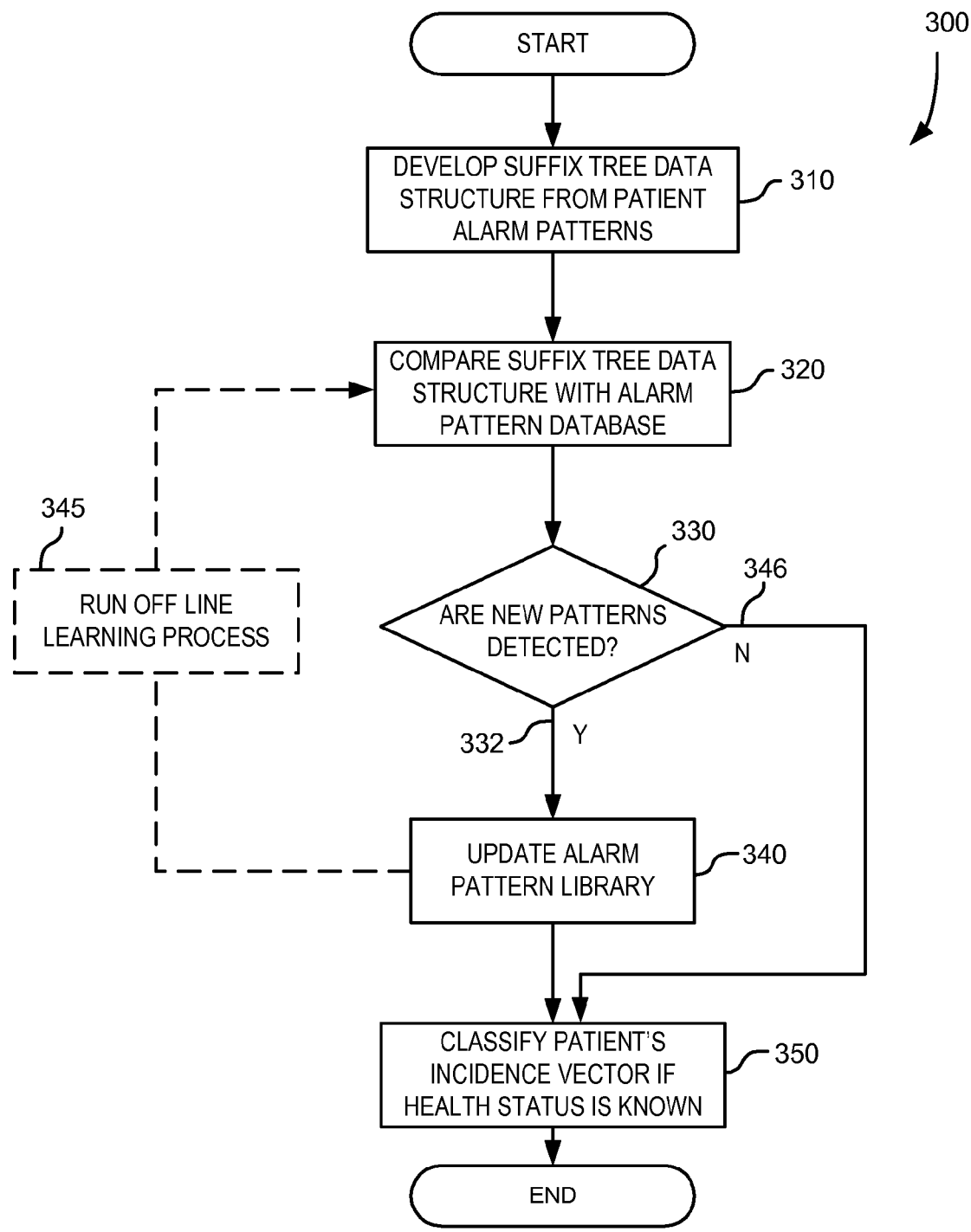
FIG. 3 is an example flowchart of an on-line method for detecting and classifying patient alarm patterns in real-time according to another embodiment of the present invention.

FIG. 3 is an example flowchart 300 of an on-line method for detecting and classifying new alarm patterns in real-time according to another embodiment of the present invention. In one example, flow chart 300 may be implemented in on-line learning module 120 and off-line learning module 118. In block 310, a suffix tree data structure is developed in real-time as alarm patterns are detected in an alarm sequence. In block 320, the suffix tree data structure is compared with an alarm pattern library 117 using a comparing algorithm to detect new alarm patterns. If a new alarm pattern is detected 332 in block 330, then the new alarm pattern type will be updated at block 340 into the alarm pattern library 117. In block 345, the off-line learning process will run when a substantial amount of new alarm patterns have been recognized to update the suffix tree data structure. In one embodiment, block 345 may be executed after every new alarm pattern type is detected. In another embodiment, block 345 may be executed after a threshold number of new alarm pattern types have been detected and stored in alarm pattern library 117. If a new alarm pattern is not detected 346 in block 330 or after the alarm pattern library 117 is updated in block 340, the incidence vector will be classified if patient's medical status or other alarm-related condition is known in block 350. More specifically, the medical status may include types of diseases, medical status of the patient, or the like. If a patient's pattern incidence vector is not recognized, it is stored for future off-line processing, and the patient is classified as "other", i.e., not similar to any previously known alarm patterns.

Figure 4:
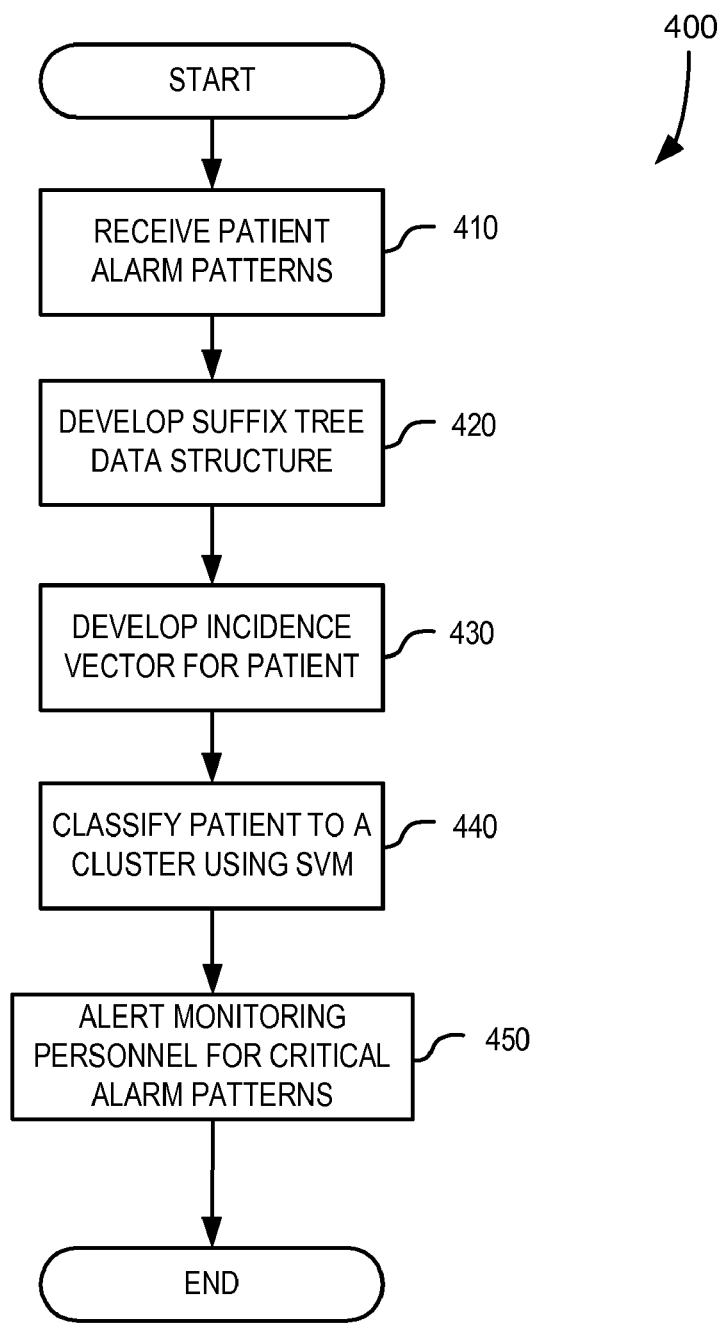
FIG. 4 is an example flowchart of a real-time method for alarm pattern detection and alerting monitoring personnel according to an embodiment of the present invention.

FIG. 4 is a flowchart 400 of a method for real-time alarm pattern detection and alerting of monitoring personnel according to an embodiment of the present invention. In one example, flow chart 400 may be implemented in on-line monitoring module 119. In block 410, an alarm sequence is received. In one example, alarm sequences may be received concurrently from multiple individual monitoring signals 114 of a patient. In another example, the monitoring signal 114 may be an interdigitated alarm signal that represents alarm events of different types and possibly for multiple physiological parameters. In block 420, as the alarm sequence progresses, a suffix tree data structure is developed in real-time to identify alarm patterns. In block 430, an incidence vector is built up in real-time in response to the suffix tree data structure. In block 440, a support vector machine algorithm is used to group the incidence vector with a cluster when sufficient alarm sequence data has been accumulated. In block 450, an alert is raised to monitoring personnel to indicate a particular classification of the patient. In one embodiment, if certain critical alarm patterns are detected early in the alarm sequence, it may be possible to classify the alarm sequence with a particular "critical" cluster/group before the end of the alarm sequence. In another embodiment, if certain critical alarm patterns are discovered in an alarm sequence, it may be possible to eliminate group/clusters that are classified with non-significant phenomena, such as, 'normal behavior,' 'stable,' and/or 'recovering.' Early classification before the alarm sequence is complete may provide prognostic value in critical conditions.

A technical contribution for the disclosed method and apparatus is that is provides for a computer implemented method for discovery, classification and detection of alarm patterns for electrophysiological monitoring systems.

Therefore, according to an embodiment of the present invention, an electrophysiological monitoring system including a plurality of sensors configured to detect one or more health parameters of a patient and a monitoring device configured to receive a plurality of sensing signals from the sensors and output a monitoring signal representative of an alarm sequence, wherein the alarm sequence comprises a set of alarm events identified in the sensing signals. The system also includes an on-line monitoring module configured to generate a suffix tree data structure in response to the monitoring signal to identify alarm patterns from the set of alarm events and classify the alarm sequence in response to the occurrences of alarm patterns in the alarm sequence. The on-line monitoring module is further configured to alert monitoring personnel of an alarm condition after processing the alarm sequence in real-time.

According to another embodiment of the present invention, a method for electrophysiological monitoring includes receiving a monitoring signal derived from a patient wherein the monitoring signal provides an alarm sequence, developing a suffix substring data structure to identify a plurality of alarm patterns from the alarm sequence, and generating an incidence vector that determines a relative incidence of each type of alarm pattern with respect to the plurality of alarm patterns in the alarm sequence. The method further includes grouping the incidence vector in a cluster using a clustering algorithm, classifying one or more patients according to their pattern incident rates which are obtained by extraction of alarm patterns and storing the classification of the incidence vector in a database.

According to yet another embodiment of the present invention, a method for electrophysiological monitoring includes receiving a monitoring signal from a patient wherein the monitoring signal provides an alarm sequence, wherein the alarm sequence includes at least one alarm pattern. The method also includes developing a suffix substring data structure in real-time to identify alarm patterns of medical interest contained in the alarm sequence and generating an incidence vector in response to the suffix substring data structure. The alarm sequence is classified to a classification cluster using a classification algorithm based on the incidence vector and monitoring personnel is alerted to indicate a condition corresponding to the cluster after processing the alarm sequence in real-time.

The present invention has been described in terms of the preferred embodiment, and it is recognized that equivalents, alternatives, and modifications, aside from those expressly stated, are possible and within the scope of the appending claims.

What is claimed is:

1. An electrophysiological monitoring system comprising:
a plurality of sensors configured to detect one or more health parameters of a patient;
a monitoring device configured to receive a plurality of sensing signals from the sensors and output a monitoring signal representative of an alarm sequence, wherein the alarm sequence comprises a set of alarm events identified in the sensing signals; and
an on-line monitoring module configured to:
generate a suffix tree data structure in response to the monitoring signal to identify alarm patterns from the set of alarm events;
classify the alarm sequence in response to the occurrences of alarm patterns in the alarm sequence; and
alert monitoring personnel of an alarm condition after processing the alarm sequence in real-time.

2. The electrophysiological monitoring system of claim 1 further comprising a real-time pattern display coupled to the monitoring station to allow viewing of the alarm sequence.

3. The electrophysiological monitoring system of claim 2 further comprising an external storage facility coupled to the monitoring station to store alarm pattern types.

4. The electrophysiological monitoring system of claim 2 further comprising an external storage facility coupled to the monitoring station to store classifications of alarm sequences.

5. The electrophysiological monitoring system of claim 2 further comprising an external storage facility which includes a database to store classifications of alarm sequences and alarm pattern types wherein the external storage facility is coupled to the monitoring station via a communications link that allows information to be accessed in real-time from the database when the alarm sequence is processed in real-time.

6. A method for electrophysiological monitoring comprising steps of:
receiving a monitoring signal derived from a patient wherein the monitoring signal provides an alarm sequence;
developing a suffix substring data structure to identify a plurality of alarm patterns from the alarm sequence;
generating an incidence vector that determines a relative incidence of each type of alarm pattern with respect to the plurality of alarm patterns in the alarm sequence;

grouping the incidence vector in a cluster using a clustering algorithm;

classifying one or more patients according to their pattern incident rates which are obtained by extraction of (possibly concurrent) alarm patterns and storing the classification of the incidence vector in a database.

7. The method of claim 6 wherein the monitoring signal includes a plurality of sensing signals that sense physiological health parameters of a patient.

8. The method of claim 6 wherein the suffix substring data structure is programmed to identify alarm patterns greater than a first length, the first length corresponding to a minimum length of an alarm pattern to be identified.

9. The method of claim 8 wherein the suffix substring data structure is programmed to identify alarm patterns in an alarm sequence between the first length and a second length, wherein the second length is greater than the first length, and wherein the second length corresponds to a maximum length of an alarm pattern to be identified.

10. The method of claim 6 further comprising associating the cluster with a patient condition using a support vector machine algorithm.

11. The method of claim 6 wherein the clustering algorithm is a K-means clustering algorithm.

12. A method for electrophysiological monitoring that detects and classifies alarm patterns comprising steps of:

receiving a monitoring signal from a patient wherein the monitoring signal provides an alarm sequence, wherein the alarm sequence includes at least one alarm pattern;

developing a suffix substring data structure in real-time to identify alarm patterns of medical interest contained in the alarm sequence;

generating an incidence vector in response to the suffix substring data structure;

classifying the alarm sequence to a classification cluster using a classification algorithm based on the incidence vector; and alerting monitoring personnel to indicate a condition corresponding to the cluster after processing the alarm sequence in real-time.

13. The method of claim 12 further comprising alerting monitoring personnel to indicate a condition when an alarm sequence is partially detected in real-time thereby allowing medical personnel to pro-actively respond to the condition before the condition worsens.

14. The method of claim 12 wherein the step of receiving the monitoring signal comprises receiving at least one physiological sensing signal derived from the patient.

15. The method of claim 12 further comprising identifying an alarm sequence greater than a first length, the first length corresponding to a minimum length of an alarm pattern to be identified.

16. The method of claim 15 wherein the suffix substring data structure is programmed to identify alarm sequences between the first length and a second length, wherein the second length is greater than the first length and corresponds to a maximum length of an alarm pattern to be identified.

17. The method of claim 12 further comprising determining the classification cluster by an unsupervised learning algorithm.

18. The method of claim 17 wherein determining comprises determining the classification cluster by a support vector machine algorithm.

19. The method of claim 12 further comprising determining the classification cluster by a supervised learning process.

20. The method of claim 19 wherein the supervised learning process is conducted by one or more qualified medical personnel.

21. The method of claim 12 further comprising identifying a new alarm pattern type in the alarm sequence in response to the generated suffix substring data structure and storing the new alarm pattern type in a database.

* * * * *